US012585721B2

(12) United States Patent
Gary, Jr.

(10) Patent No.: US 12,585,721 B2
(45) Date of Patent: Mar. 24, 2026

(54) SINGLE BARCODE SCAN CAST SYSTEM FOR PHARMACEUTICAL PRODUCTS

(71) Applicant: ConsortiEX Inc., Milwaukee, WI (US)

(72) Inventor: Wyndham Fairchild Gary, Jr., Mequon, WI (US)

(73) Assignee: ConsortiEX Inc., Milwaukee, WI (US)

( * ) Notice: Subject to any disclaimer, the term of this patent is extended or adjusted under 35 U.S.C. 154(b) by 475 days.

(21) Appl. No.: 17/941,898

(22) Filed: Sep. 9, 2022

(65) Prior Publication Data

US 2024/0086486 A1 Mar. 14, 2024

(51) Int. Cl.
*G16H 40/20* (2018.01)
*G06F 16/955* (2019.01)
(Continued)

(52) U.S. Cl.
CPC ....... *G06F 16/9554* (2019.01); *G06K 7/1434* (2013.01); *G06Q 30/0623* (2013.01); *G16H 10/60* (2018.01); *G16H 40/20* (2018.01)

(58) Field of Classification Search
CPC .... G06F 16/9554; G16H 40/20; G16H 10/60; G06K 7/1434; G06Q 30/0623
(Continued)

(56) References Cited

U.S. PATENT DOCUMENTS

| | | | | |
|---|---|---|---|---|
| 6,457,049 | B2 * | 9/2002 | Lewis | G16H 20/10 |
| | | | | 718/100 |
| 8,099,339 | B1 | 1/2012 | Pinsonneault et al. | |

(Continued)

FOREIGN PATENT DOCUMENTS

WO WO-2019178031 A1 * 9/2019 ............. G16H 40/20

OTHER PUBLICATIONS

Extended European Search Report for Application No. 23195239.1 dated Jan. 22, 2024 (20 pages).
(Continued)

*Primary Examiner* — Christopher L Gilligan
*Assistant Examiner* — Jessica Marie Webb
(74) *Attorney, Agent, or Firm* — Michael Best & Friedrich LLP

(57) ABSTRACT

Systems and methods for distributing pharmaceutical product information. The system includes a transmitter device and a receiver device. The transmitter device includes a first electronic processor and first communications interface communicatively connected to both of a barcode scanner and to a first electronic communications device. The receiver device includes a second electronic processor and a second communications interface communicatively connected to a second electronic communications device. The first electronic processor is configured to receive from the barcode scanner, via the first communications interface, scanned product information of a product, and transmit the scanned product information to the receiver device. The second electronic processor is configured to receive the scanned product information, determine, from the scanned product information, a subset of product information relevant to a software application of the second electronic communications device, and transmit, to the second electronic communications device, the subset of product information.

8 Claims, 4 Drawing Sheets

(51) Int. Cl.

| | |
|---|---|
| *G06K 7/14* | (2006.01) |
| *G06Q 30/0601* | (2023.01) |
| *G16H 10/60* | (2018.01) |

(58) Field of Classification Search

USPC ........................................................ 705/2, 3

See application file for complete search history.

(56) References Cited

U.S. PATENT DOCUMENTS

| | | | |
|---|---|---|---|
| 8,412,538 | B2 | 4/2013 | Hardaway |
| 9,904,965 | B2 | 2/2018 | White et al. |
| 10,002,273 | B1 | 6/2018 | Dreselly Thomas et al. |
| 10,868,676 | B2 | 12/2020 | Nguyen et al. |
| 11,551,800 | B1 * | 1/2023 | Bartos .................. G06K 7/1417 |
| 2010/0084849 | A1 * | 4/2010 | Masuda .............. G06F 16/9554 283/67 |
| 2010/0332257 | A1 * | 12/2010 | Sims ...................... G16H 10/60 705/2 |
| 2011/0257991 | A1 | 10/2011 | Shukla |
| 2012/0136698 | A1 * | 5/2012 | Kent .................. G06Q 20/3276 705/14.1 |
| 2016/0140315 | A1 | 5/2016 | Diaz et al. |
| 2016/0171258 | A1 | 6/2016 | Reitstaetter |
| 2017/0098060 | A1 | 4/2017 | Schneider et al. |
| 2018/0068078 | A1 * | 3/2018 | Barthell .................. G06N 20/00 |
| 2018/0349974 | A1 * | 12/2018 | Dutta .................. G06F 16/9554 |
| 2019/0034872 | A1 | 1/2019 | Sullivan |
| 2020/0005237 | A1 * | 1/2020 | Simons .............. G06Q 10/0832 |
| 2020/0098460 | A1 | 3/2020 | Banks et al. |

OTHER PUBLICATIONS

Jones, "Drug Supply Chain Security Act of 2013 and It's Computer System Implementation," EWU Masters Thesis Collection, 2014, pp. 1-132.

Sarkar, "Supply Chain Security Act 2023: Interoperable Data Exchange for Drug Traceability," International Journal of Scientific Research in Computer Science, Engineering and Information Technology, 2022, vol. 8, Issue 3, pp. 471-477.

European Union, "Regulation (EU) 2016/679 of the European Parliament and of the Council of Apr. 27, 2016," Official Journal of the European Union, 2016, 88 pages.

Anonymous, "QR Code," Wikipedia <https://web.archive.org/web/20200101080048/https://en.wikipedia.org/wiki/QR_code> web page dated Dec. 29, 2019 (28 pages).

European Patent Office Examination Report for Application No. 23195239.1 dated Feb. 6, 2026 (10 pages).

Motorola, Inc., "Symbol DS6707 Digital Image Scanner," Product Reference Guide, dated Oct. 2008 (394 pages).

IHE International, Inc., "IHE Pharmacy Technical Framework Supplement Uniform Barcode Processing (UBP)," Rev. 1.1—Trial Implementation, dated Dec. 4, 2017 (30 pages).

* cited by examiner

*102*

SINGLE BARCODE SCAN CAST SYSTEM FOR PHARMACEUTICAL PRODUCTS

BACKGROUND OF THE INVENTION

Pharmacies, hospitals, and other medical facilities receive, store, and distribute numerous types of medication to patients. Handling medications requires, among other things, complying with certain regulations (for example, the Drug Supply Chain Security Act or DSCSA). The DSCSA include requirements for managing and electronically tracing certain prescription drugs that are handled and distributed by dispensing machines (or dispensers). Certain information regarding each prescription drug may be required to be electronically stored and updated from reception to distribution.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments, examples, and aspects of concepts that include the claimed subject matter and explain various principles and advantages of those embodiments, examples, and aspects.

Figure 1:
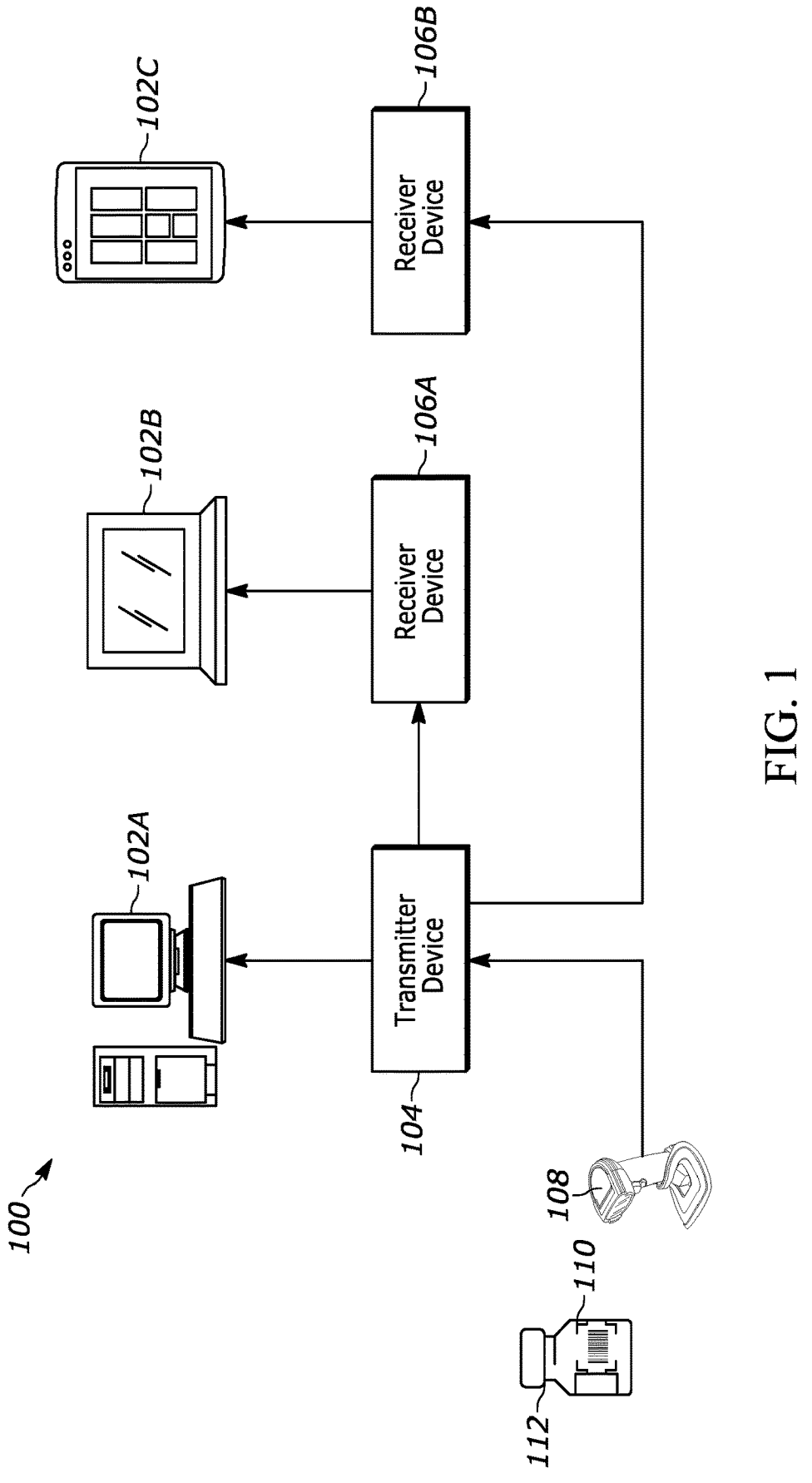
FIG. 1 illustrates a pharmaceutical product information system in accordance with some examples.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of examples, aspects, and features illustrated.

In some instances, the apparatus and method components have been represented where appropriate by conventional symbols in the drawings, showing only those specific details that are pertinent to understanding the certain, examples, features, and aspects so as not to obscure the disclosure with details that will be readily apparent to those of ordinary skill in the art having the benefit of the description herein.

DETAILED DESCRIPTION OF THE INVENTION

As noted, certain regulations require the collection and storage of particular information for certain pharmaceutical products, particularly prescription drugs (for example, in order to trace a product from reception to distribution to a patient). Typically, such information is gathered from a barcode label of the product via a barcode scanner. The scanner, following a scan, provides the information to an electronic communications device (for example, a computer, an electronic tablet, etc.), which then uses the information to populate one or more digital forms. The forms (and the information thereof) may then be stored in one or more of a local and/or remote database.

Medical professionals and other staff of a facility (for example, a pharmacy) may have to scan a barcode of a single product numerous times between different electronic communications devices in order to collect and store particular information and forms according to regulations, as each device may have different software applications to fulfill certain purposes (for example, different forms) and not others. Numerous scans of a single product may be time-consuming and may lead to mistakes. While certain facilities may implement a system where information collected from a single scan is provided to a shared network (for example, to a cloud network or a local server/device) that the other devices of the facility have access to, such configurations may be expensive and time-consuming in set-up and implementation.

To address these problems and for other reasons, systems and methods are provided herein for, among other things, managing and distributing barcode information of a pharmaceutical product, collected from a single scan, to a plurality of different electronic communication devices within a common facility. In particular, a single scan is performed and the collected product information is transmitted (i.e. cast) to one or more additional communication devices. Using such systems and methods, the number of manual barcode scans for a common product is reduced without the need to implement a more complicated, expensive system. The examples, aspects, and features provide an easy, inexpensive set-up that may be readily modified to add or remove devices of the system. The examples, aspects, and features described herein also provide a system that is easily transferable and adaptable. In addition, and as explained in more detail below, the embodiments, examples, aspects, and feature allow for continued use of software applications configured to process information from a one-dimensional barcode (for example, older applications) within a system despite the fact that pharmaceutical product barcodes are increasingly two-dimensional.

One example provides a pharmaceutical product information system. The system includes a transmitter device and a receiver device. The transmitter device includes a first electronic processor and first communications interface communicatively connected to both of a barcode scanner and to a first electronic communications device. The receiver device includes a second electronic processor and a second communications interface communicatively connected to a second electronic communications device. The first electronic processor is configured to receive from the barcode scanner, via the first communications interface, scanned product information of a product, and transmit the scanned product information to the receiver device. The second electronic processor is configured to receive, via the second communications interface, the scanned product information, determine, from the scanned product information, a subset of product information relevant to a software application of the second electronic communications device, and transmit, to the second electronic communications device, the subset of product information.

For ease of description, some or all of the example systems presented herein are illustrated with a single exemplar of each of its component parts. Some examples may not describe or illustrate all components of the systems. Other examples may include more or fewer of each of the illustrated components, may combine some components, or may include additional or alternative components.

It should be understood that although certain figures presented herein illustrate hardware and software located within particular devices, these depictions are for illustrative purposes only. In some embodiments, the illustrated components may be combined or divided into separate software, firmware, and/or hardware. For example, instead of being located within and performed by a single electronic processor, logic and processing may be distributed among multiple electronic processors. Regardless of how they are combined or divided, hardware and software components may be located on the same computing device or may be distributed among different computing devices connected by one or more networks or other suitable communication links.

It should also be understood that, while the examples are described herein in regard to pharmaceutical products, the systems and methods described may be applied to different scannable items (for example, other regulated products).

FIG. 1 is a diagram of one example system 100, which is configured to, among other things, manage and distribute barcode information of a pharmaceutical product, collected from a single scan, to a plurality of different electronic communication devices within a common facility. In the example illustrated, the system 100 includes a plurality of electronic communications devices 102A-102C (singularly referred to herein as an electronic communications device 102), an electronic transmitter device 104, a plurality of electronic receiver devices 106A and 106B (singularly referred to herein as an electronic receiver device 106), and a barcode scanner 108. The system 100 may include more components than those illustrated. In particular, it should be understood that, although FIG. 1 illustrates only three communications devices 102A-102C, a single transmitter device 104, and two receiver devices, the system 100 may include additional communications devices, transmitter devices, receiver devices, and scanners.

As illustrated, the electronic transmitter device 104 is communicatively connected (via a suitable wired or wireless connection or some combination thereof) to the electronic communications device 102A, the scanner 108, and at least one of the electronic receiver devices 106A and 106B. Each of the electronic receiver devices 106A and 106B is also communicatively connected to a respective electronic communications device 102B and 102C via a suitable wired or wireless connection. The wireless communications between one or more components of the system 100 may be implemented using various local and wide area networks, for example, a Bluetooth™ network or a Wi-Fi™ network, the Internet, or combinations or derivatives thereof.

Figure 3:
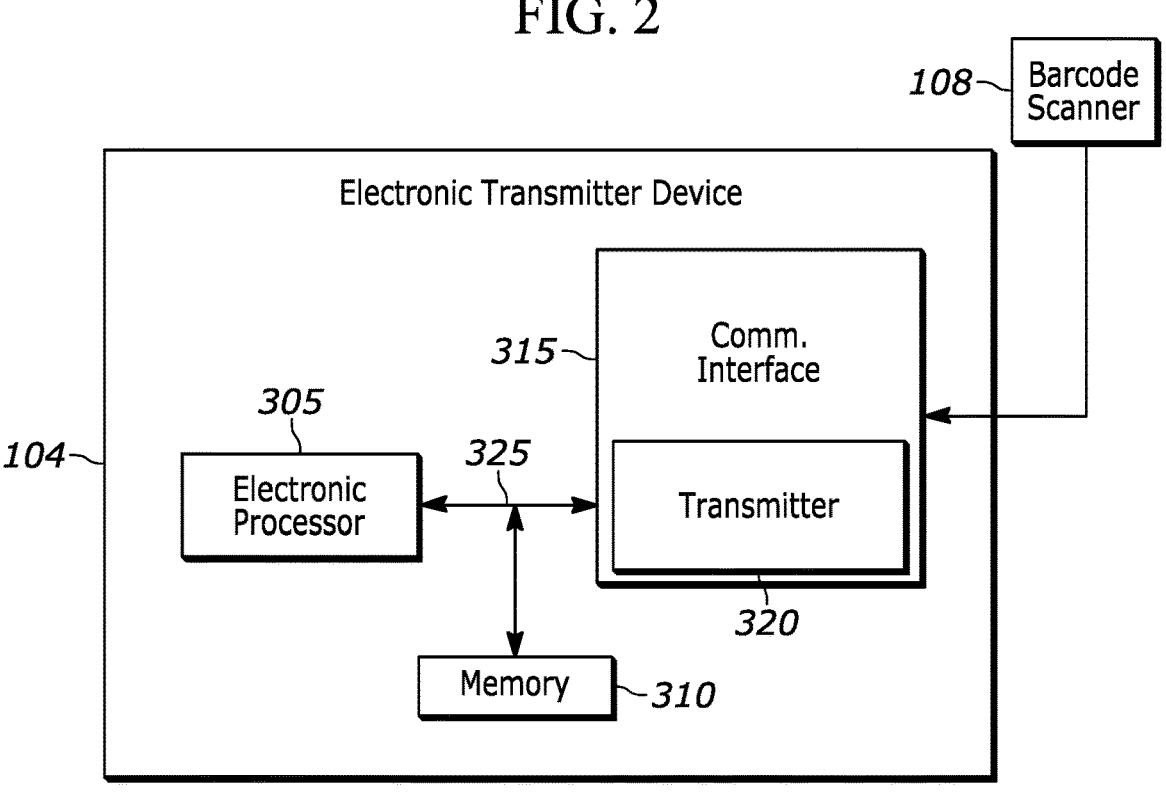
FIG. 3 is a diagram of an electronic transmitter device of the system of FIG. 1 in accordance with some examples.

The electronic communications devices 102A-102C, described more particularly with respect to FIG. 3, are electronic devices configured to execute or run at least one software application that uses product information scanned (for example, via the barcode scanner 108) from a barcode 110 (which may be one-dimensional or two-dimensional) of (or related to) a pharmaceutical product 112. The barcode 110 may be for a single pharmaceutical product 112 (for example, a prescription bottle containing medicine therein) or of a package containing multiple products 112 (for example, a container including a plurality of prescription bottles). Each software application run by a respective electronic communications device 102A-102C may require different product information. For example, a software application of the electronic communications device 102A may require information regarding a wholesaler of the product 112 whereas a software application of the electronic communications device 102B may require an expiration date of the product 112.

The electronic communications devices 102A-102C may be, for example, a computer, a laptop, an electronic tablet, a cellular phone, and the like. In some instances, the electronic communications devices 102A-102C may be different types of devices. For example, as illustrated in FIG. 1, the device 102A is a desktop computer, the device 102B is a laptop, and the device 102C is an electronic tablet. In some instances, the electronic communications devices 102A-102C are all the same type of device.

In the illustrated example, each of the electronic communications devices 102A-102C are not directly communicatively connected to each other. In some instances, at least one of the electronic communications devices 102A-102C is configured to be a single or limited input or input/output communications device that can only be connected to a single device or a limited number of electronic devices (for example, to the transmitter device 104 or to a respective receiver device 106A, 106B). In some instances, at least one of the electronic communications devices 102B and 102C is communicatively connected to an additional scanner.

The transmitter device 104, as mentioned above, is communicatively connected to the barcode scanner 108. The barcode scanner 108 is configured to scan the barcode 110 of the product 112 to collect information about the product 112. The product information may include, for example, a national drug code (NDC), a serial number, a primary manufacturer, a secondary manufacturer, a handling history, inventory information, a product weight, a product quantity/count, a patient identity, a manufacturing date, a received date, an expiration date, content information, a prescribing physician identity, side effect information, price information, a lot code, a drug strength, a prescribed dosage, a product name, and the like. The product information is provided from the scanner to the electronic transmitter device 104. As explained in more detail below, the transmitter device 104 is configured to process the received product information and not only forward a subset of the product information to the electronic communications device 102A in which the device 104 is directly coupled to, but also forwards the complete product information to at least one other electronic receiver device (for example, either or both of the receiver devices 106A and 106B). Each receiver device 106A, 106B that receives the product information also processes the information to determine a subset of information necessary for a respective application of the respective electronic communications device 102B, 102C in which the receiver device 106A, 106B is communicatively connected to. In some embodiments, one or more of the receiver devices 106A, 106B may also be communicatively coupled to a respective barcode scanner (not shown).

Figure 2:
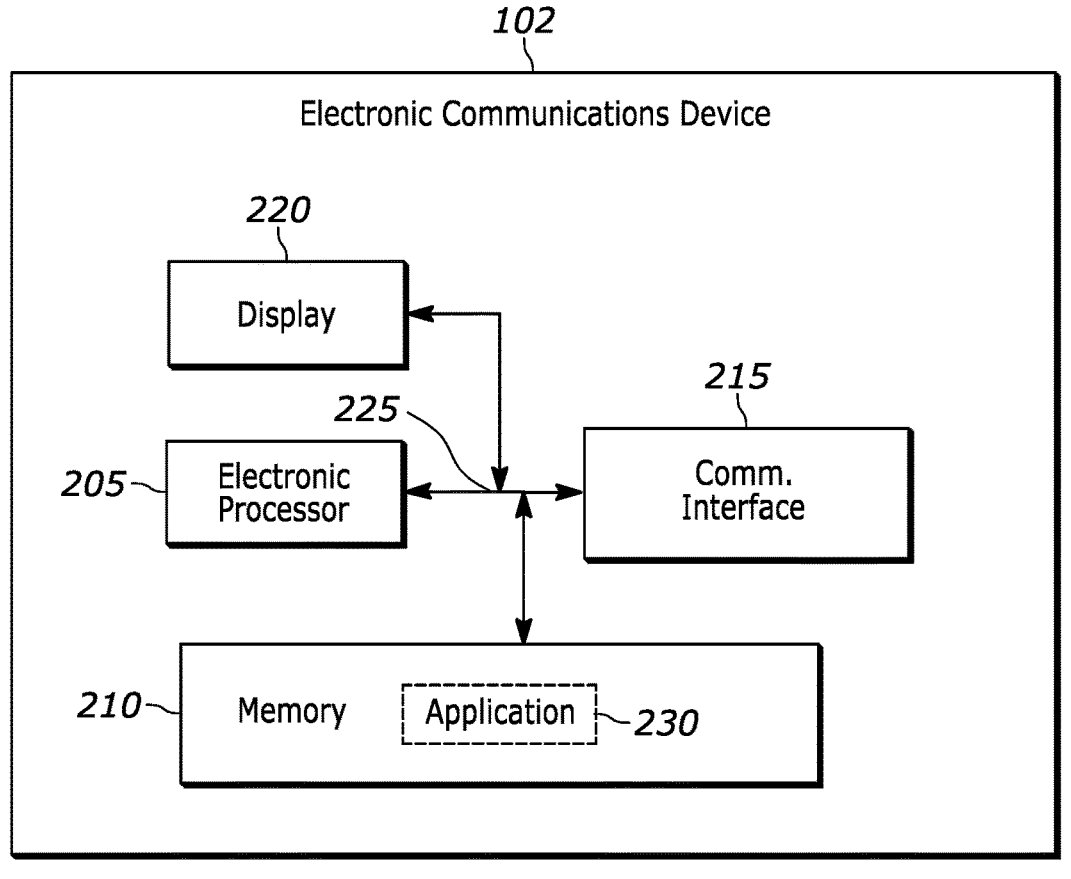
FIG. 2 is a diagram of an electronic communications device of the system of FIG. 1 in accordance with some examples.

FIG. 2 schematically illustrates one example embodiment of an electronic communications device 102. In the embodiment illustrated, the electronic communications device 102 includes an electronic processor 205, a memory 210, a communication interface 215, and a display 220. The illustrated components, along with other various modules and components are connected to each other by or through one or more control or data buses (for example, the bus 225) that enable communication therebetween.

The electronic processor 205 may include one or more microprocessors, an application-specific integrated circuit (ASIC), or another suitable electronic device. The electronic processor 205 obtains and provides information (e.g., to and from the memory 210 and/or the communication interface 215) and processes the information by executing one or more software instructions or modules, capable of being stored, for example, in a random access memory ("RAM")

area of the memory 210, a read only memory ("ROM") of the memory 210, or another non-transitory computer readable medium (not shown). The software can include firmware, one or more applications, program data, filters, rules, one or more program modules, and other executable instructions. In the example illustrated, the memory 210 stores, among other things, a software application 230.

The electronic processor 205 is configured to retrieve from the memory 210 and execute, among other things, software related to processes and methods described herein. The electronic processor 205 executes instructions stored in the memory 210 to implement functionality of the software application 230. The software application 230 may include a data form application configured to populate a form based on product information received from a respectively connected device (either the transmitter device 104 or the receiver device 106) and display the form via a graphical user interface (GUI) on the display 220.

The electronic processor 205 is configured to control the communication interface 215 to transmit and receive communication signals to and from at least one other device (for example, the transmitter device 104 or the receiver device 106). The communications interface 215 may include various digital and analog components (for example, digital signal processors, high band filters, low band filters, and the like), which for brevity are not described herein and which may be implemented in hardware, software, or a combination of both. The communications interface 215 may include, for example, a transceiver, a transmitter, and/or a receiver (not shown). The communication interface 215 may alternatively or additionally include one or more ports (for example, a universal serial bus port or USB, an Ethernet port, etc.) for wired communications with a respective device (for example, the electronic transmitter device 104 or the electronic receiver device 106).

The display 220 is a suitable display, such as a liquid crystal display (LCD) screen, an organic light-emitting diode (OLED) screen, and the like. As mentioned above, in some embodiments, the electronic processor 205 may generate a populated data form based on received product information and display the form through a GUI on the display 220.

The electronic communications device 102 may include aspects of a human machine interface (e.g., a keypad, switches, buttons, soft keys, indictor lights (e.g., light emitting diodes), and the like) for interacting with the electronic communications device 102.

FIG. 3 schematically illustrates one example of an electronic transmitter device 104. In the example illustrated, the electronic transmitter device 104 includes an electronic processor 305, a memory 310, and a communication interface 315 including a transmitter 320. The illustrated components, along with other various modules and components are connected to each other by or through one or more control or data buses (for example, the bus 325) that enable communication therebetween.

The electronic processor 305, the memory 310, and the communication interface 315 may be configured and function similar to the electronic processor 205, the memory 210, and the communication interface 215 respectively. However, the memory 310 differs in that it does not store a software application 230 for generating a form. Rather, the memory 310 stores instructions, which are executed by the electronic processor 305, for processing product information received from the barcode scanner 108 to determine and transmit a subset of product information to the electronic communications device 102A based on the particular application 230 of the electronic communications device 102A. The processor 305 also is configured to transmit (either directly or via a broadcast) the scanned product information to one or more receiver devices 106 (for example, via the transmitter 320). In some instances, the transmitter device 104 includes a receiver (not shown) for wirelessly receiving information from another device (for example, from the barcode scanner 108). The receiver may be integrated with the transmitter 320 in the form of a transceiver.

Figure 4:
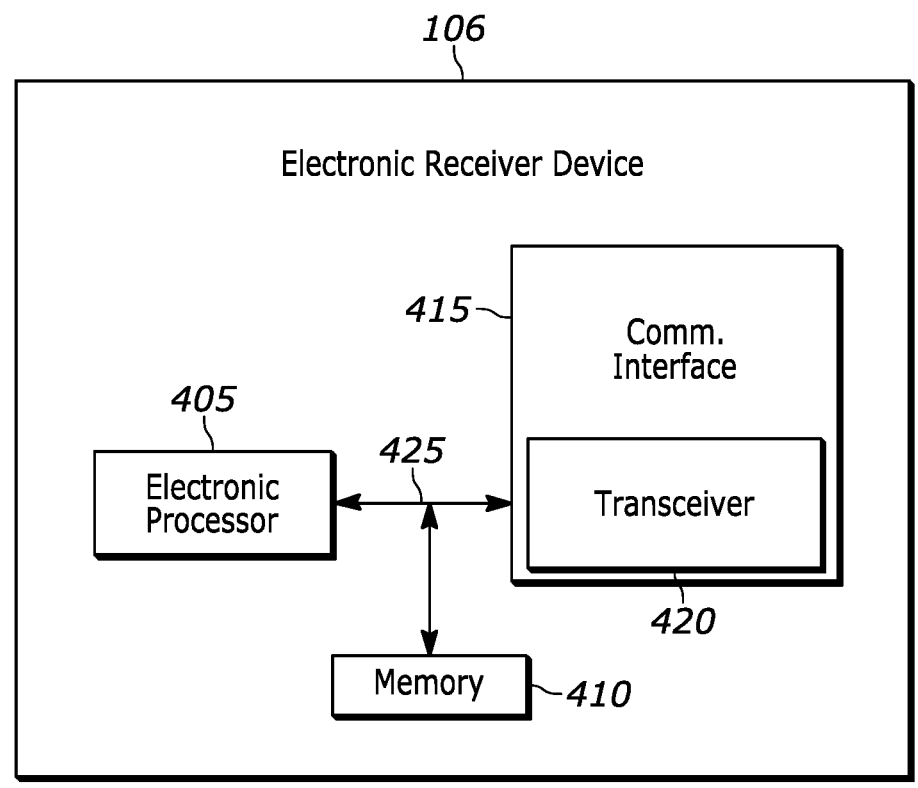
FIG. 4 is a diagram of an electronic receiver device of the system of FIG. 1 in accordance with some examples.

FIG. 4 schematically illustrates one example of an electronic receiver device 106. In the example illustrated, the electronic receiver device 106 includes an electronic processor 405, a memory 410, and a communication interface 415 including a receiver 420 configured to receive product information (for example, from the transmitter device 104). The illustrated components, along with other various modules and components are coupled to each other by or through one or more control or data buses (for example, the bus 425) that enable communication therebetween.

The electronic processor 405, the memory 410, and the communication interface 415 may be configured and function similar to the electronic processor 305, the memory 310, and the communication interface 315 respectively. However, the memory 410 stores instructions, which are executed by the electronic processor 405, for processing product information received from the transmitter device 104 (instead of from a barcode scanner directly) to determine and transmit a subset of product information to an electronic communications device 102A the receiver device 106 is communicatively connected to (for example, electronic communications device 102B or 102C) based on the particular application 230 of the respective electronic communications device 102. Furthermore, in some instances, the receiver device 106 may not be configured to transmit the scanned product information to one or more receiver devices 106. However, in some instances, the receiver device 106 may be configured to transmit received information to one or more additional receiver devices 106. In some examples, the receiver device 106 includes a transmitter (not shown) for wirelessly transmitting information to another device (for example, to the electronic communications device 102 and/or to another receiver device 106). The transmitter may be integrated with the receiver 420 in the form of a transceiver. In some embodiments, the receiver device 106 is communicatively coupled to a barcode scanner (not shown) and is configured to utilize product information received from the scanner. The product information may be processed by the electronic processor 405 and provided (completely or in part) to the respective electronic communications device 102 and/or additional devices as described below.

Figure 5:
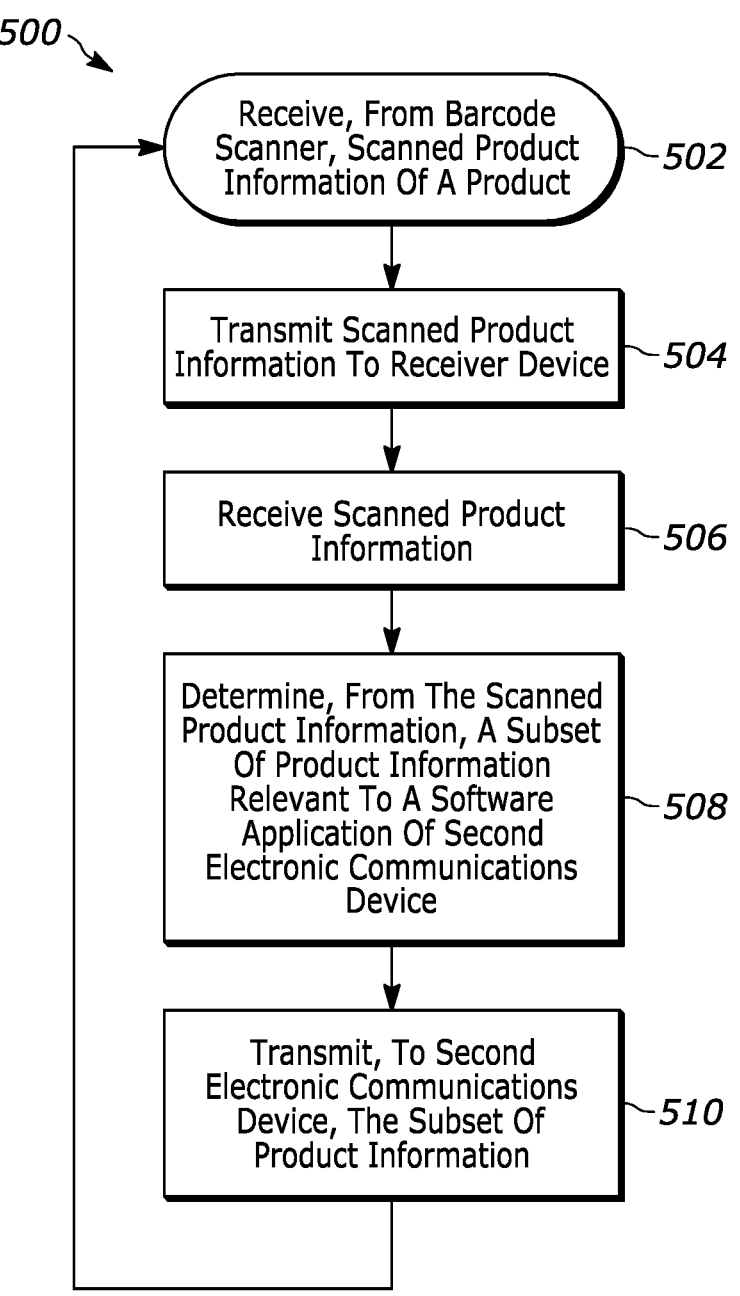
FIG. 5 is a flowchart illustrating a method for processing information collected from a barcode of a pharmaceutical product implemented by the system of FIG. 1 in accordance with some examples.

FIG. 5 illustrates an example method 500 for processing information collected from a barcode (for example, the barcode 110) of a pharmaceutical product (for example, the product 112). Although the method 500 is described in conjunction with the system 100 as described herein, the method 500 may be used with other systems and devices. In addition, the method 500 may be modified or performed differently than the specific example provided.

By way of example, the method 500 is described as being performed by the electronic transmitter device 104 and the electronic receiver device 106B (in particular, the electronic processors 305 and 405 respectively). However, it should be understood that, in some examples, the method 500 may be performed differently. For example, in some instances, the electronic transmitter device 104 and receiver device 106 (and the functionality thereof) may be integrated into a single electronic communications device (for example, the electronic communications device 102A or a separate device). In such cases, the method 500 may be implemented on a single electronic processor. In addition, even though the method 500 is described in terms of a single transmitter device and a single receiver device, the method 500 may be performed with systems that include multiple receiver devices.

Furthermore, as generally described above, it should be understood that the transmissions and receptions of information described below may be performed wired or wirelessly or some combination thereof.

The method 500 begins, at block 502, with the electronic processor 305 receiving from the barcode scanner 108, via the communication interface 315 (for example, via a wired connection or wirelessly via the transmitter 320), scanned product information of the product 108. In particular, the product information is a data string including one or more data contents (elements) derived from the barcode 110 of the product 112. At block 504, the electronic processor 305 transmits the scanned product information to the receiver device 106B. In some cases, as mentioned above, the electronic processor 305 may transmit the product information to an additional receiver device (for example receiver device 106C) in parallel (simultaneously) to the transmission of product information to the receiver device 106B.

At block 506, the electronic processor 405 of the receiver device 106B receives, via the communication interface 315, the product information from the transmitter device 104. At block 508, the electronic processor 405 of the receiver device 106B determines, from the scanned product information, a subset of product information relevant to a software application (for example, the application 230 of the electronic communications device 102B) of the electronic communications device 102B. The subset of product information is the data string derived from the barcode 110 with at least one data element removed. The electronic processor 405 of the receiver device 106B then transmits the subset of product information to the electronic communications device 102B (block 510). The electronic communications device 102B may then generate, via the software application 230, a GUI based on the subset of product information relevant to the software application 230 of the second electronic communications device 102B and display the GUI on the display 220.

In some cases, following block 502, the electronic processor 305 of the transmitter device 104 is configured to determine, from the scanned product information, a subset of product information relevant to a software application 230 of the electronic communications device 102A and transmit the subset of product information to the electronic communications device 102A. The electronic communications device 102A may then also generate, via the software application 230, a GUI based on the subset of product information relevant to the software application 230 of the electronic communications device 102A and display the GUI on its respective display 220. As mentioned above, the subset of product information transmitted to the electronic communications device 102A may be different than the subset of product information transmitted to the other electronic communications device(s) 102B, 102C depending on information required by the software application 230 of the respective device 102. This saves time and processing required by the respective electronic communications device 102. It should be understood that, in some instances, depending on the particular application 230 of the respective electronic communications device, the complete received product information may be provided to the device 102B by the respective transmitter device 104/receiver device 106.

In the determination of the subset of product information, the respective device (the transmitter device 104 or receiver device 106) is configured to convert the data elements of the barcode 110 into a data string readable by the respective electronic communications device 102. As mentioned above, the barcode 110 may be a one-dimensional or two-dimensional barcode. A particular software application 230 of the electronic communications device 102, in some instances, is configured to handle data strings derived from one-dimensional barcodes and not two-dimensional barcodes. Such software applications 230 may only require a single element of product information derived from the barcode 110. For example, the software application 230 may require an NDC of the product 112. In instances where the barcode 110 is a one-dimensional barcode, the NDC may be the only element of product information that can be derived from the barcode 110. In instances where the barcode 110 is a two-dimensional barcode, a scan of the barcode may collect the NDC as well as additional elements of product information (for example, a lot code, an expiration date, a serial number, etc.). In such latter instances, the resulting data string, if sent to the electronic communications device 102 containing all elements collected from the scan, may not be able to be processed properly by software applications 230 that are configured to receive and process only single element data strings of one-dimensional barcodes. Thus, to enable continued functionality of the particular software application 230, the respective device (the transmitter device 104 or receiver device 106) is configured to remove the additional elements from the data string during processing such that a data string containing only a single element (for example, the NDC) is sent to the electronic communications device 102.

In some cases, the electronic processor 305 (and/or the electronic processor 405) is configured to determine a number of times in which scanned product information of a plurality of products 112 of a common type has been received from the barcode scanner 108 and transmit the number of times to one or more of the receiver devices 106. This information may be provided to one or more of the electronic communications devices 102 as inventory information if required by the respective software application 230. In some embodiments, the electronic processor 305 is configured to send additional information along with the product information to one or more of the receiver devices 106. For example, the transmitter device 104 may transmit product information (or a subset thereof) to the electronic communications device 102A. The electronic communications device 102A may utilize the received information to retrieve (for example, from a local or remote database) or determine additional information regarding the product 112 of the scanned barcode 110 (for example, a purchase order number). The electronic communications device 102B may transmit this additional information to the transmitter device 104. The transmitter device 104 may then transmit/cast the additional information to one or more of the receiver devices 106.

In the foregoing specification, various embodiments, examples, aspects, and features have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of the present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing," or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about," or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (for example, comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

Various features and advantages of some embodiments are set forth in the following claims.

I claim:

1. A pharmaceutical product information system, the system comprising:

a barcode scanner configured to perform a scan of a barcode of a product;

a transmitter device including a first electronic processor and first communications interface communicatively connected to (i) the barcode scanner via a first wired connection implementing a one-way one-to-one communication protocol and to (ii) a first electronic communications device via a second wired connection implementing a one-way serial communication protocol; and a first receiver device including a second electronic processor and a second communications interface communicatively connected to a second electronic communications device via a third wired connection implementing a one-way serial communication protocol;

wherein the first electronic processor is configured to:

receive from the barcode scanner, via the first communications interface and the first wired connection, a multidimensional code including scanned product information of the product from the scan, convert the multidimensional code into a first readable data string including a plurality of data elements representing a full set of scanned product information, parse the first readable data string to determine a first readable subset of the plurality of data elements comprising a first single element of scanned product information, wherein the first readable subset of the plurality of data elements is capable of being processed by a first software application executing at the first electronic communications device, derive a second readable data string including the first readable subset of the plurality of data elements, transmit, to the first electronic communications device via the second wired connection, the second readable data string including the first readable subset of the plurality of data elements via the wired, one-way serial communication protocol, wherein the full set of scanned product information is not transmitted to the first electronic communications device, and transmit the first readable data string including the full set of scanned product information to the first receiver device via a fourth wired connection implementing a one-way one-to-many communication protocol;

wherein the second electronic processor of the first receiver device is configured to:

receive, via the fourth wired connection and the second communications interface, the first readable data string including the plurality of data elements representing the full set of scanned product information, parse the first readable data string to determine a second readable subset of the plurality of data elements comprising a second single element of scanned product information, wherein the second readable subset of the plurality of data elements is capable of being processed by a second software application executing at the second electronic communications device, derive a third readable data string including the second readable subset of the plurality of data elements, and transmit, to the second electronic communications device via the third wired connection, the third readable data string including the second readable subset of the plurality of data elements, wherein the full set of scanned product information is not transmitted to the second electronic communications device;

wherein the first electronic communications device includes a first display and is configured to generate and display, via the first software application, a first graphical user interface based on the first readable subset of the plurality of data elements;

wherein the second electronic communications device includes a second display and is configured to generate and display, via the second software application, a second graphical user interface based on the second readable subset of the plurality of data elements; and wherein the transmitter device, the receiver device, the first electronic communications device, and the second electronic communications device are not servers.

2. The system of claim 1, wherein the first readable subset of the plurality of data elements represents product information that is different from product information represented by the second readable subset of the plurality of data elements.

3. The system of claim 1, wherein the first readable subset of the plurality of data elements represents product information that is the same as product information represented by the second readable subset of the plurality of data elements.

4. The system of claim 1, wherein the second electronic processor is further configured to determine a number of times in which scanned product information of a plurality of products of a common type has been received from the barcode scanner.

5. The system of claim 1, wherein the first electronic processor is further configured to transmit the first readable data string to a second receiver device in parallel with transmitting the first readable data string to the first receiver device.

6. The system of claim 1, wherein the first software application and the second software application are each configured to process a single-element data string derived from two-dimensional barcode data.

7. The system of claim 1, wherein the first electronic processor is configured to derive the second readable data string by removing a data element from the first readable data string.

8. The system of claim 1, wherein the first electronic processor is configured to derive the second readable data string by converting a two-dimensional barcode data string into a single element data string.

* * * * *